United States Patent
Boudjema et al.

(10) Patent No.: US 10,813,667 B1
(45) Date of Patent: Oct. 27, 2020

(54) VACUUM DRIVEN IMPLANTATION DEVICE

(71) Applicants: Pascal Boudjema, Paris (FR); William R Rassman, Los Angeles, CA (US)

(72) Inventors: Pascal Boudjema, Paris (FR); William R Rassman, Los Angeles, CA (US)

( * ) Notice: Subject to any disclaimer, the term of this patent is extended or adjusted under 35 U.S.C. 154(b) by 0 days.

(21) Appl. No.: 16/827,137

(22) Filed: Mar. 23, 2020

(51) Int. Cl.
*A61B 17/34* (2006.01)
*A61F 2/10* (2006.01)
*A61B 10/02* (2006.01)
*A61B 17/00* (2006.01)

(52) U.S. Cl.
CPC ...... *A61B 17/3468* (2013.01); *A61B 10/0283* (2013.01); *A61F 2/10* (2013.01); *A61B 2017/00544* (2013.01); *A61B 2017/00561* (2013.01); *A61B 2017/00752* (2013.01); *A61B 2017/00969* (2013.01)

(58) Field of Classification Search
CPC ...... A61B 17/3468; A61B 17/34–3498; A61B 10/0283; A61F 2/10
USPC ....................................................... 606/187
See application file for complete search history.

(56) References Cited

U.S. PATENT DOCUMENTS

| | | | | |
|---|---|---|---|---|
| 5,439,475 A | * | 8/1995 | Bennett | A61B 17/3468 606/187 |
| 5,827,297 A | * | 10/1998 | Boudjema | A61B 10/0283 606/133 |
| 7,452,367 B2 | | 11/2008 | Rassman et al. | 606/187 |
| 2008/0167674 A1 | * | 7/2008 | Bodduluri | A61M 5/20 606/187 |
| 2014/0343575 A1 | * | 11/2014 | Andreani | A61B 17/3468 606/132 |
| 2016/0015424 A1 | * | 1/2016 | Kim | A61B 17/3468 606/187 |
| 2016/0120574 A1 | * | 5/2016 | Shiao | A61F 2/10 606/187 |

FOREIGN PATENT DOCUMENTS

WO    WO/2020/065144    4/2020

* cited by examiner

*Primary Examiner* — Katrina M Stransky
*Assistant Examiner* — Brigid K Byrd
(74) *Attorney, Agent, or Firm* — Venable LLP

(57) ABSTRACT

A device and system for implanting a hair graft, the device having an elongated body; an intermediate reservoir operably coupled to an anterior end of the elongated body and extending axially therefrom; a skin abutment piece movably coupled to an anterior end of the intermediate reservoir; and a beveled hollow needle operably coupled to an anterior end of the skin abutment piece. The system also includes a source of pressure operably coupled to the device; a hair graft container operably coupled to the device; a vacuum source operably coupled to the device; a differential pressure detector operably coupled to the device; and a controller in communication with the source of pressure, the hair graft container, the vacuum source, and the differential pressure detector.

30 Claims, 11 Drawing Sheets

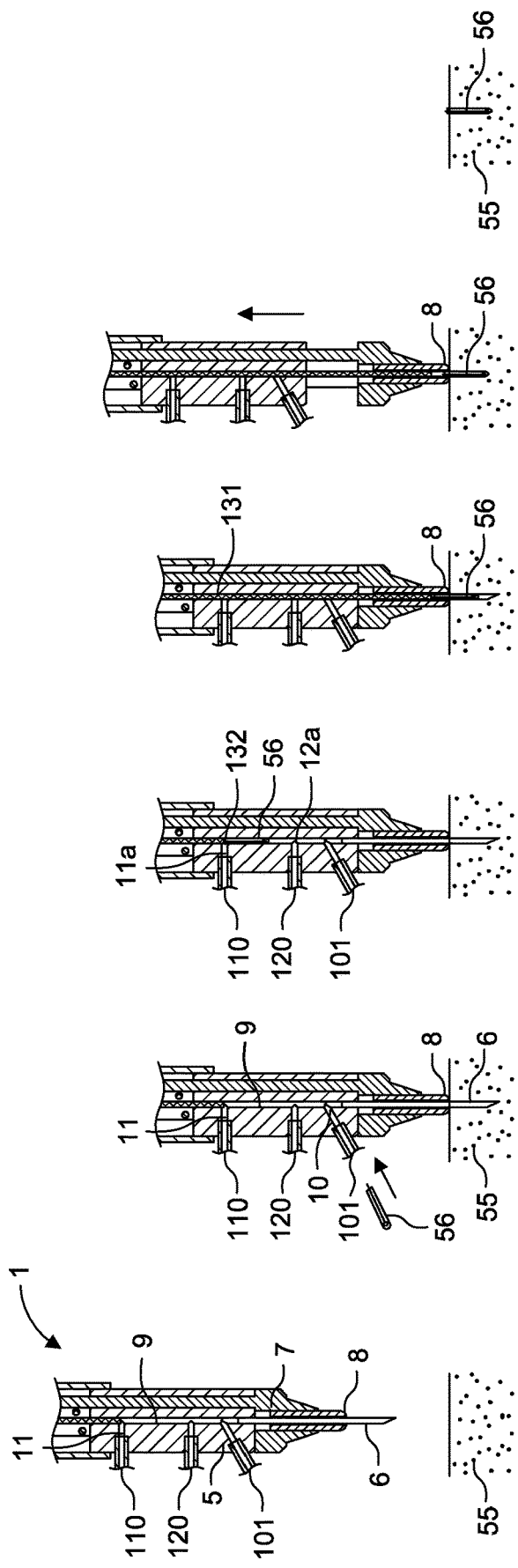

VACUUM DRIVEN IMPLANTATION DEVICE

BACKGROUND

1. Technical Field

The field generally relates to a device and system for implanting a hair graft, and methods of use thereof.

2. Discussion of Related Art

Follicular unit excision (FUE) is a process by which individual follicular units are harvested for implantation at an incision site on the scalp. Current practice for handling harvested follicular units includes forceps to hold and implant harvested follicular units. However, practitioners recognize that handling fragile harvested follicular units and implanting them using forceps could jeopardize the growth of the follicular units by applying unnecessary stress upon them. In addition, the current practice of hair transplantation involves the creation of an incision site followed by the implantation of a harvested follicular unit into the incision site. This process is then repeated until the desired or required amount of harvested follicular units have been implanted into a target area. Such a process is often labor intensive and time consuming. Thus, there remains a need for a device and system that simultaneously reduces damage to the harvested follicular unit and allows for the rapid loading and implanting of the harvested follicular units.

SUMMARY

An embodiment of the instant disclosure herein relates to a device for implanting a hair graft, having: an elongated body comprising an internal channel and a posterior plug configured to be operably coupled to a tube; an intermediate reservoir operably coupled to an anterior end of the elongated body and extending axially therefrom. In such an embodiment, the intermediate reservoir includes: an internal longitudinal central axis channel stretching over an entire length of the intermediate reservoir, the internal longitudinal central axis channel being fluidly connected at a posterior end to an anterior end of the internal channel, and being configured to accept and contain a hair graft; an anterior opening disposed on the intermediate reservoir and proximal to an anterior end of the intermediate reservoir; an anterior channel configured to allow a passage of the hair graft from the anterior opening and through an anterior orifice to the internal longitudinal channel; a posterior opening disposed on the intermediate reservoir and anterior to a posterior end of the intermediate reservoir; a posterior channel configured to open perpendicularly into the internal longitudinal central axis channel from the posterior opening and through a posterior orifice; an accessory opening disposed on the intermediate reservoir and between the anterior opening and the posterior opening; and an accessory channel configured to open perpendicularly into the internal longitudinal central axis channel from the accessory opening and through an accessory orifice. The device also includes a skin abutment piece movably coupled to the anterior end of the intermediate reservoir; and a beveled hollow needle operably coupled to an anterior end of the skin abutment piece. In such an embodiment, the skin abutment piece is configured to allow passing of the hair graft from the internal longitudinal central axis channel to a lumen of the beveled hollow needle, the elongated body further comprises an actuatable rectilinear rod in the internal channel, the actuatable rectilinear rod being of a sufficient length to slide from the internal longitudinal central axis channel over an entire length of the beveled hollow needle, the actuatable rectilinear rod being movable between a first position for facilitating loading of the hair graft into the internal longitudinal central axis channel where the posterior orifice is partially obstructed by an anterior end of the actuatable rectilinear rod, and a second position where the anterior end of the actuatable rectilinear rod occupies the lumen of the beveled hollow needle, and the actuatable rectilinear rod, when in the second position, is configured to displace the hair graft from the internal longitudinal central axis channel, through the lumen, and through a tip of the beveled hollow needle.

An embodiment of the instant disclosure herein relates to a system for implanting a hair graft, having: the device for implanting a hair graft discussed above; a source of pressure operably coupled to the posterior plug; a hair graft container operably coupled to the anterior opening; a vacuum source operably coupled to the posterior opening; a differential pressure detector operably coupled to the accessory opening; and a controller in communication with the source of pressure, the hair graft container, the vacuum source, and the differential pressure detector.

An embodiment of the instant disclosure relates to a method for implanting a hair graft into a scalp using the device discussed above, the method including the steps of: creating a vacuum in the longitudinal central axis channel; obstructing the beveled hollow needle by inserting the beveled hollow needle into the scalp; loading the hair graft into the internal longitudinal central axis channel by passaging the hair graft from a hair graft container, through the anterior opening, through the anterior orifice, and into the internal longitudinal channel; detecting the hair graft in the internal longitudinal central axis channel; and actuating the actuatable rectilinear rod such that the actuatable rectilinear rod displaces the hair graft from the internal longitudinal central axis channel, through the lumen, and through the tip of the beveled hollow needle.

An embodiment of the instant disclosure relates to a hair graft storage tray having a plurality of hair graft storage wells. Each of the plurality of hair graft storage wells is configured to ensure that the hair grafts are properly oriented. In some embodiments, proper orientation includes storage of the hair grafts in a root-down orientation. In addition, the hair graft storage tray is configured to be operably coupled to a hair graft reservoir.

BRIEF DESCRIPTION OF THE DRAWINGS

Further objectives and advantages will become apparent from a consideration of the description, drawings, and examples.

FIGS. 5A-5F are sectional views illustrating different successive stages respectively of the loading of a hair graft into the implantation instrument of FIG. 1 as well as of the implantation of the hair graft into the skin.

DETAILED DESCRIPTION

Figure 1:
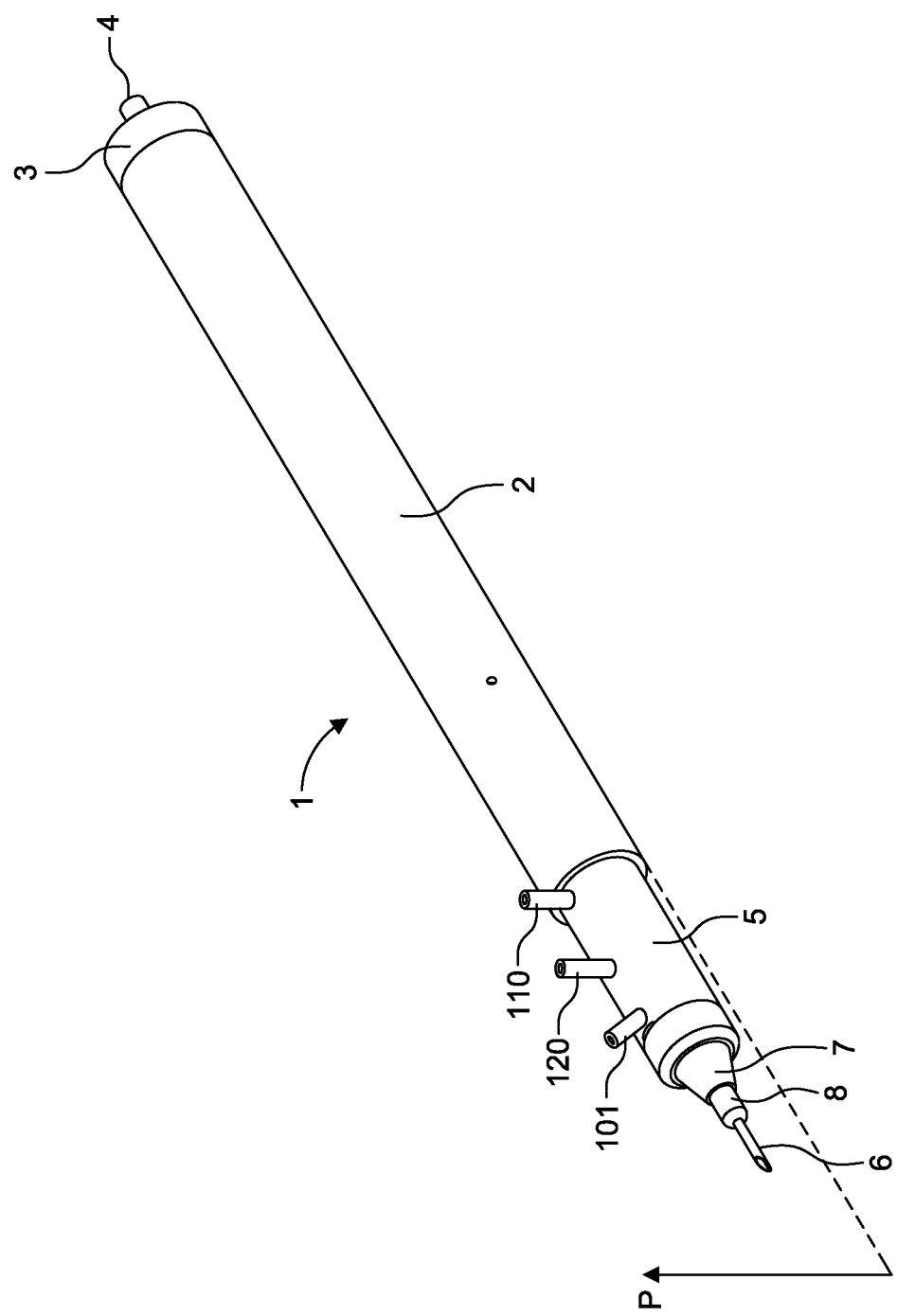
FIG. 1 is a perspective view of a device for implanting hair grafts into a scalp according to an embodiment of the disclosure.

Some embodiments of the current disclosure herein are discussed in detail below. In describing embodiments, specific terminology is employed for the sake of clarity. However, the disclosure herein is not intended to be limited to the specific terminology so selected. A person skilled in the relevant art will recognize that other equivalent components can be employed and other methods developed without departing from the broad concepts of the current disclosure herein. All references cited anywhere in this specification, including the Background and Detailed Description sections, are incorporated by reference as if each had been individually incorporated.

The terms "graft" and "hair graft" are used interchangeably throughout. In general, the terms "graft" and "hair graft" refer to any piece of hair-bearing tissue that can be implanted. A harvested graft is a piece of hair-bearing tissue that has been removed from one area and is to be implanted or otherwise transplanted into a separate area. Methods of harvesting hair grafts are known in the art.

The terms "subject" and "patient" are used interchangeably throughout. In general, the terms "subject" and "patient" refer to an individual in need of or in want of a hair transplantation procedure.

The term "target tissue" as used throughout refers to a tissue location to be targeted for a hair implantation procedure. In many of the embodiments disclosed herein, the target tissue is a region on the scalp of a patient or subject. However, the target tissue is not limited to the scalp of a patient or subject and can include other areas of the patient's or subject's epidermis and underlying dermis.

The terms "hair graft container" and "hair graft reservoir" are used interchangeably throughout and refer to a receptacle for storing multiple hair grafts and is separate from a device for implanting a hair graft. In some embodiments, the hair graft container or reservoir includes a hair graft storage tray.

The term "controller" refers to a component configured to interact with and at least partially command operation of various components including, but not limited to a source of pressure, a hair graft container, a vacuum source, and a differential pressure detector. The controller commands operation of various components at least in part based on information received from one or more of the various components. In some embodiments, the controller comprises a processor and/or a software component.

Device

An embodiment of the instant disclosure relates to a device for implanting a hair graft, including: an elongated body having an internal channel and a posterior plug configured to be operably coupled to a tube; an intermediate reservoir operably coupled to an anterior end of the elongated body and extending axially therefrom. The intermediate reservoir includes: an internal longitudinal central axis channel stretching over an entire length of the intermediate reservoir, the internal longitudinal central axis channel being fluidly connected at a posterior end to an anterior end of the internal channel, and being configured to accept and contain a hair graft; an anterior opening disposed on the intermediate reservoir and proximal to an anterior end of the intermediate reservoir; an anterior channel configured to allow a passage of the hair graft from the anterior opening and through an anterior orifice to the internal longitudinal channel; a posterior opening disposed on the intermediate reservoir and anterior to a posterior end of the intermediate reservoir; and a posterior channel configured to open into the internal longitudinal central axis channel from the posterior opening and through a posterior orifice. The device also includes a skin abutment piece movably coupled to the anterior end of the intermediate reservoir; and a hollow needle operably coupled to an anterior end of the skin abutment piece. The skin abutment piece is configured to allow passing of the hair graft from the internal longitudinal central axis channel to a lumen of the hollow needle, the elongated body further includes an actuatable rectilinear rod in the internal channel, the actuatable rectilinear rod being of a sufficient length to slide from the internal longitudinal central axis channel over an entire length of the hollow needle, the actuatable rectilinear rod being movable between a first position for facilitating loading of the hair graft into the internal longitudinal central axis channel where the posterior orifice is partially obstructed by an anterior end of the actuatable rectilinear rod, and a second position where the anterior end of the actuatable rectilinear rod occupies the lumen of the hollow needle, and the actuatable rectilinear rod, when in the second position, is configured to displace the hair graft from the internal longitudinal central axis channel, through the lumen, and through a tip of the hollow needle.

In embodiments as described above and throughout, the "posterior opening" and "posterior orifice" are distinct structures separated by a "posterior channel". The posterior opening permits access to a first end of the posterior channel, while the posterior orifice connects a second end of the posterior channel to a longitudinal channel of the intermediate reservoir of the device.

In embodiments as described above and throughout, the "anterior opening" and "anterior orifice" are distinct structures separated by an "anterior channel". The anterior opening permits access to a first end of the anterior channel, while the anterior orifice connects a second end of the anterior channel to a longitudinal channel of the intermediate reservoir of the device.

An embodiment of the disclosure relates to the device above, where the intermediate reservoir further includes: an accessory opening disposed on the intermediate reservoir and between the anterior opening and the posterior opening; and an accessory channel configured to open perpendicularly into the internal longitudinal central axis channel from the accessory opening and through an accessory orifice.

An embodiment of the disclosure relates to the device above, where the posterior opening and the accessory opening are spaced at least 10 mm apart.

An embodiment of the disclosure relates to the device above, where the posterior channel is configured to open perpendicularly into the internal longitudinal central axis channel from the posterior opening and through a posterior orifice.

An embodiment of the disclosure relates to the device above, where the hollow needle is a beveled hollow needle.

An embodiment of the disclosure relates to the device above, where the intermediate reservoir further includes a hollow slide stretching over an entire length of the intermediate reservoir, and the skin abutment piece is movably coupled to the anterior end of the intermediate reservoir including a rigid axis, the rigid axis being connected at an anterior end to the posterior end of the skin abutment piece, the rigid axis being configured to pass through the hollow slide, and the rigid axis being connected at a posterior end to the anterior end of the elongated body.

An embodiment of the disclosure relates to the device above, where moving of the actuatable rectilinear rod to the first position results in moving of the skin abutment piece to a first skin abutment piece position where the skin abutment piece is in contact with the intermediate reservoir, and where moving of the actuatable rectilinear rod to the second position results in moving of the skin abutment piece to a second skin abutment piece position where the intermediate reservoir is separated from the skin abutment piece in an axial direction by the rigid axis.

An embodiment of the instant disclosure herein relates to a device for implanting a hair graft, having: an elongated body including an internal channel and a posterior plug configured to be operably coupled to a tube; an intermediate reservoir operably coupled to an anterior end of the elongated body and extending axially therefrom. In such an embodiment, the intermediate reservoir includes: an internal longitudinal central axis channel stretching over an entire length of the intermediate reservoir, the internal longitudinal central axis channel being fluidly connected at a posterior end to an anterior end of the internal channel, and being configured to accept and contain a hair graft; an anterior opening disposed on the intermediate reservoir and proximal to an anterior end of the intermediate reservoir; an anterior channel configured to allow a passage of the hair graft from the anterior opening and through an anterior orifice to the internal longitudinal channel; a posterior opening disposed on the intermediate reservoir and anterior to a posterior end of the intermediate reservoir; a posterior channel configured to open perpendicularly into the internal longitudinal central axis channel from the posterior opening and through a posterior orifice; an accessory opening disposed on the intermediate reservoir and between the anterior opening and the posterior opening; and an accessory channel configured to open perpendicularly into the internal longitudinal central axis channel from the accessory opening and through an accessory orifice. The device also includes a skin abutment piece movably coupled to the anterior end of the intermediate reservoir; and a beveled hollow needle operably coupled to an anterior end of the skin abutment piece. In such an embodiment, the skin abutment piece is configured to allow passing of the hair graft from the internal longitudinal central axis channel to a lumen of the beveled hollow needle, the elongated body further includes an actuatable rectilinear rod in the internal channel, the actuatable rectilinear rod being of a sufficient length to slide from the internal longitudinal central axis channel over an entire length of the beveled hollow needle, the actuatable rectilinear rod being movable between a first position for facilitating loading of the hair graft into the internal longitudinal central axis channel where the posterior orifice is partially obstructed by an anterior end of the actuatable rectilinear rod, and a second position where the anterior end of the actuatable rectilinear rod occupies the lumen of the beveled hollow needle, and the actuatable rectilinear rod, when in the second position, is configured to displace the hair graft from the internal longitudinal central axis channel, through the lumen, and through a tip of the beveled hollow needle.

An embodiment of the instant disclosure herein relates to the device discussed above, where the intermediate reservoir further includes a hollow slide stretching over an entire length of the intermediate reservoir, and where the skin abutment piece is movably coupled to the anterior end of the intermediate reservoir including a rigid axis, the rigid axis being connected at an anterior end to the posterior end of the skin abutment piece, the rigid axis being configured to pass through the hollow slide, and the rigid axis being connected at a posterior end to the anterior end of the elongated body.

An embodiment of the instant disclosure herein relates to the device discussed above, where moving of the actuatable rectilinear rod to the first position results in moving of the skin abutment piece to a first skin abutment piece position where the skin abutment piece is in contact with the intermediate reservoir, and where moving of the actuatable rectilinear rod to the second position results in moving of the skin abutment piece to a second skin abutment piece position where the intermediate reservoir is separated from the skin abutment piece in an axial direction by the rigid axis.

An embodiment of the instant disclosure herein relates to the device discussed above, where the posterior opening and the accessory opening are spaced at least 10 mm apart.

An embodiment of the instant disclosure relates to a device for implantation of a hair graft to an implantation depth at an implantation site in a patient's scalp including: a hollow needle through which the hair graft is implantable to the implantation site; a skin abutment piece at least partially around the hollow needle, the skin abutment piece being movable between a first position in which the hollow needle projects beyond the skin abutment piece by the implantation depth and a second position in which the skin abutment piece is substantially flush with a tip of the hollow needle, where a spring biases the skin abutment piece to the first position; and a rod slidably positioned inside the hollow needle and constructed to advance the hair graft through the hollow needle while the hollow needle is inserted to the implantation depth at the implantation site and while the skin abutment piece is in the first position. In such an embodiment, the skin abutment piece is moved to the second position after implantation of the hair graft through the hollow needle to the implantation depth, so as to withdraw the hollow needle from the implantation site leaving the hair graft implanted at the implantation site at the implantation depth.

An embodiment of the instant disclosure herein relates to the device discussed above, further including a piston for advancing the rod through the needle, where the skin abutment piece extends longitudinally inward of the device to a posterior end thereof, and where the piston has a stop positioned longitudinally to engage with the posterior end of the skin abutment piece move the skin abutment piece from the first position to the second position.

An embodiment of the instant disclosure herein relates to the device discussed above, where the piston is spring loaded so as to be biased against engagement of the stop to the posterior end of the skin abutment piece.

An embodiment of the instant disclosure herein relates to the device discussed above, further including a port constructed to receive pressurized gas so as to drive the piston against the bias of its spring loading.

An embodiment of the instant disclosure herein relates to a device for implantation of a hair graft to an implantation depth at an implantation site in a patient's scalp including: a reservoir constructed to receive the hair graft; a hollow needle extending outwardly of the device from an anterior end of the reservoir; a movable rod biased to a first position at a posterior end of the reservoir, the rod being slidably positionable inside the hollow needle and constructed to advance the hair graft through the hollow needle to the implantation depth while the hollow needle is inserted at the implantation site; an accessory channel which opens to the interior of the reservoir, the accessory channel being positioned away from the first position toward the hollow needle at a distance substantially corresponding to a length of the hair graft; a rear channel which opens to the interior of the reservoir, the rear channel being positioned substantially adjacent to the first position. In such an embodiment, a vacuum source connected to the rear accessory channel aspirates the hair graft into the reservoir responsive to placement of the hollow needle adjacent the patient's scalp, and a detector connected to the accessory channel provides an indication that the hair graft is aspirated to the reservoir response to detection of a pressure change at the accessory channel.

An embodiment of the instant disclosure herein relates to the device discussed above, further including an oblique channel through which the hair graft is aspirated, the oblique channel being angled obliquely relative to the reservoir and being positioned between the accessory channel and the hollow needle.

An embodiment of the instant disclosure herein relates to the device discussed above, where the indication is comprised of at least one of multiple signals including audible, visual and electronic control signals.

An embodiment of the instant disclosure herein relates to the device discussed above, where responsive to the indication, a source of pressure drives the movable rod from the first position to a second position where the hair graft is advanced through the hollow needle to the implantation depth while the hollow needle is inserted at the implantation site.

FIG. 1 is a perspective view of a device for implanting hair grafts into a scalp according to an embodiment of the disclosure.

Figure 2:
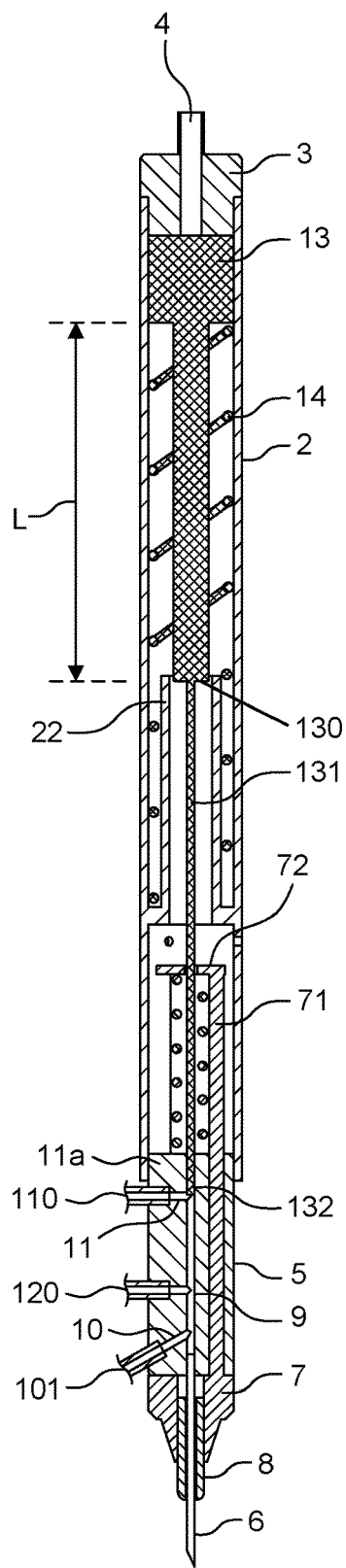
FIG. 2 is a sectional view of the embodiment of FIG. 1 along the plane P.

FIG. 2 is a sectional view of the embodiment of FIG. 1 along the plane P.

Figure 3A:
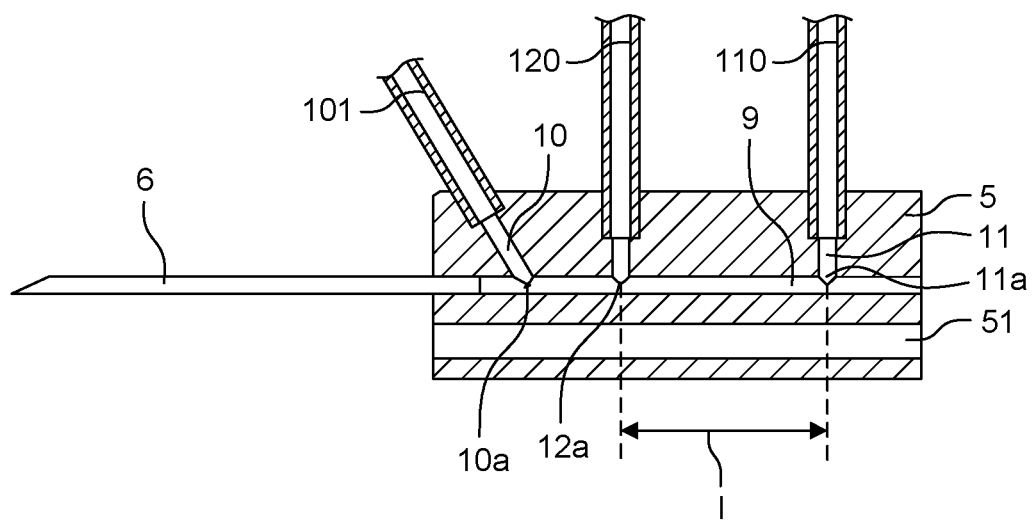
FIG. 3A and FIG. 3B are enlarged sectional views of the graft intermediate storage tank of the embodiment of FIG. 1.
Figure 3B:
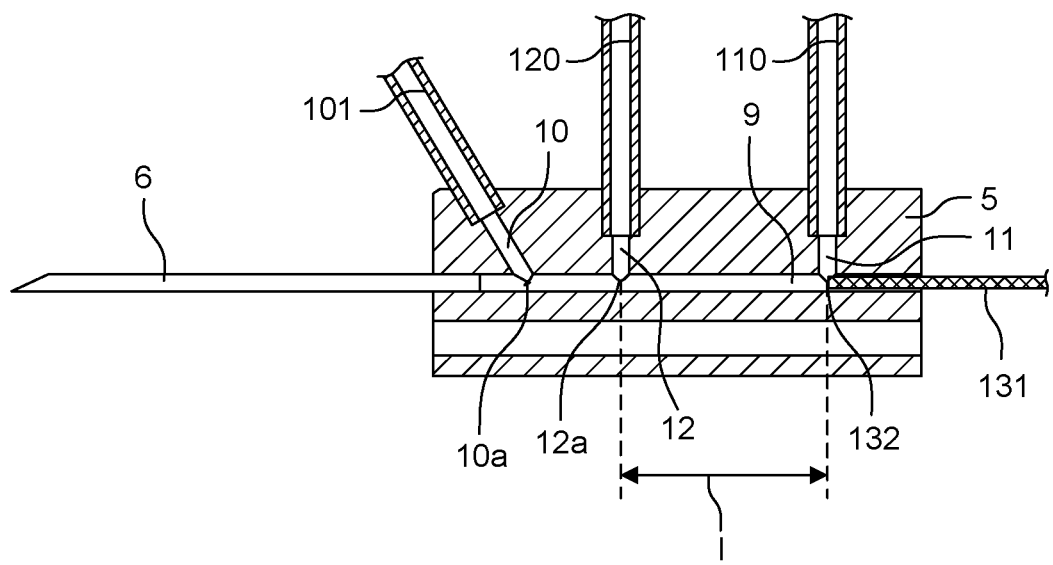

FIG. 3A and FIG. 3B are enlarged sectional views of the graft intermediate storage tank of the embodiment of FIG. 1.

As illustrated in FIGS. 1, 2, 3A and 3B, a hair implantation device 1 according an embodiment of the disclosure includes an elongated body 2 of hollow cylindrical shape having a posterior plug 3 and a connection means 4 to a tube (not shown) connected to a source of compressed air. The device 1 has, at its front, a piece of cylindrical shape acting as an intermediate reservoir 5 of a graft extended axially in front by a beveled hollow needle 6. The intermediate reservoir 5 is extended forward by a movable piece of conical shape acting as a skin abutment 7 by means of a hollow screw acting as a skin abutment head 8 adjustable relative to the part 7. The intermediate reservoir 5 has over its entire length a longitudinal central axial channel 9 of cylindrical shape, the diameter is suitable for receiving and containing a hair graft. The reservoir 5 has at its front part a first oblique anterior channel 10, suitable for the passage of a graft opening into the central channel 9 through an orifice (or anterior opening) 10a of diameter substantially identical to that of the central channel. The reservoir 5 has at its rear part a second rear (or posterior) channel 11 opening perpendicularly into the central channel 9 through an orifice (or posterior opening) 11a. The reservoir 5 has a third accessory channel 12 located between the oblique channel 10 and the posterior channel 11. The accessory channel 12 opens perpendicularly into the central channel 9 through an orifice (or accessory opening) 12a. The orifices 11a and 12a are spaced a minimum distance "I" greater than the length of a graft, or approximately 10 mm. The oblique anterior channel 10 is connected at a distance by a flexible tube 101 to a hair graft reservoir (see FIGS. 8 and 9). The posterior channel 11 is connected remotely by a flexible tube 110 to a vacuum source (see FIGS. 8 and 9). The accessory channel 12 is connected remotely by a flexible tube 120 to a differential pressure detector (see FIGS. 8 and 9) connected to the tube 110.

The cylindrical body 2 includes a piston 13 movable inside the body according to a predefined stroke. The piston 13 is extended forward by a stop 130 itself extended by a central rectilinear cylindrical rod 131 of approximately 1 mm in diameter and of sufficient length suitable for sliding in leak-tight manner in the central channel 9 and over the entire length of the needle 6. The length of the rod 131 is configured so that its free anterior end 132 comes to be positioned precisely with regard to the orifice 11a by partially obstructing it so that the orifice 11a can both let fluids (air or water) pass freely in the channel 11 and block a hair graft (not shown) in the central channel 9, when the piston 13 is in the rest or withdrawal position in the body 2. The piston 13 is mobilized in forward position within the body 2 over a predefined distance "L" until it comes into contact with the stop 22 of the body 2 when a source of compressed air (see FIGS. 8 and 9) is applied at the level of the connection means 4. A return spring 14 allows the piston 13 to return to its rear rest position when the compressed air source is cut off.

Figure 6A:
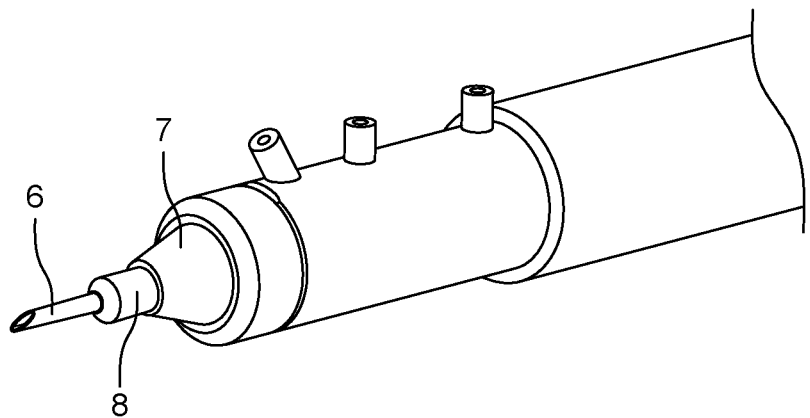
FIG. 6A and FIG. 6B are partial detail views of the front part of the implantation device of FIG. 1 in the rest position and in the action position.
Figure 6B:
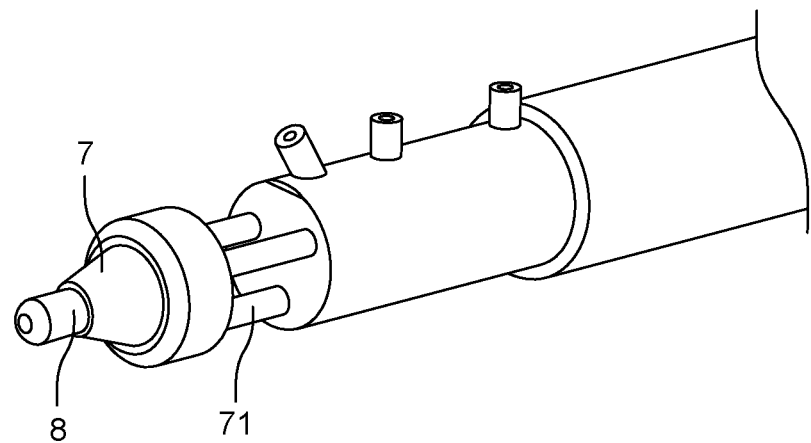
Figure 7:
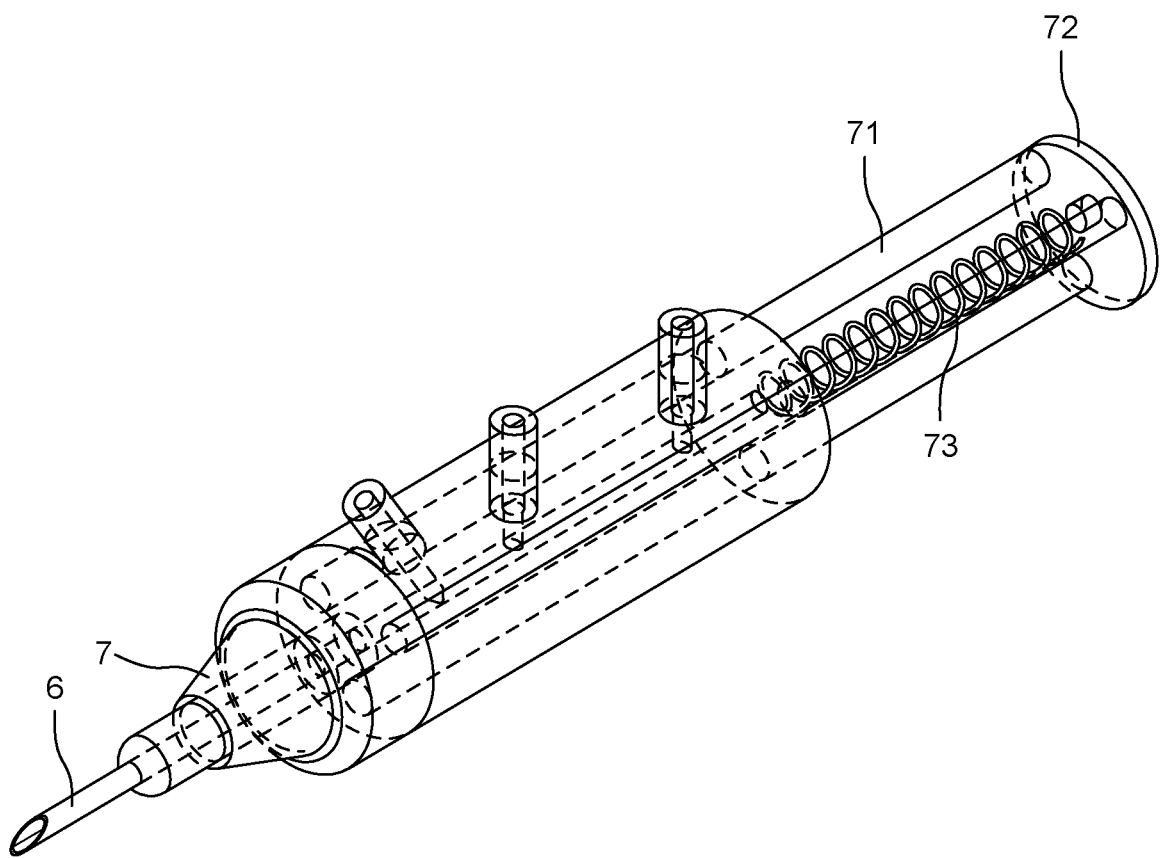
FIG. 7 is a detailed perspective view of the implantation head and the skin abutment device according to the embodiment of FIG. 1.

The skin abutment piece 7 disposed at the front of the body 2 is configured to move longitudinally relative to the intermediate reservoir 5 by means of at least one eccentric rigid axis 71 of cylindrical shape parallel to the central channel 9, sliding along a hollow slide 51 of the same diameter as described in FIG. 3A as well as in FIGS. 6A, 6B and 7. The rigid axis 71 is configured to be moved forwards over a distance of approximately 10 mm slightly greater than the free length of the needle 6 when the stop 130 of the piston 13 comes into contact with the posterior end 72 of the skin stop 7.

Figure 4C:
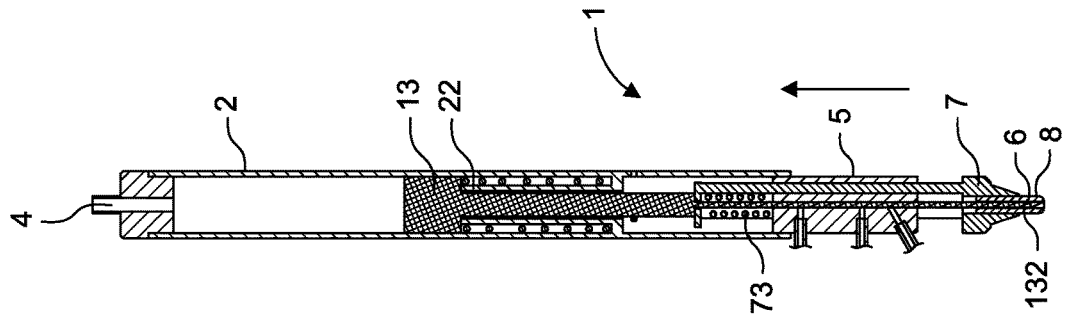
FIGS. 4A-4C are sectional views according to FIG. 2 illustrating the position of the constituent elements of the implantation device of FIG. 1 in the rest position and in the action position.
Figure 4B:
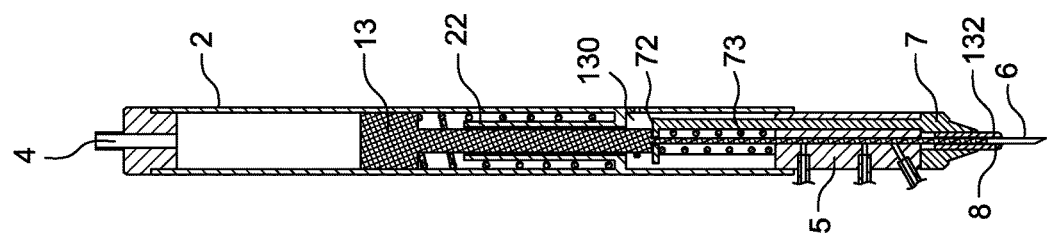
Figure 4A:
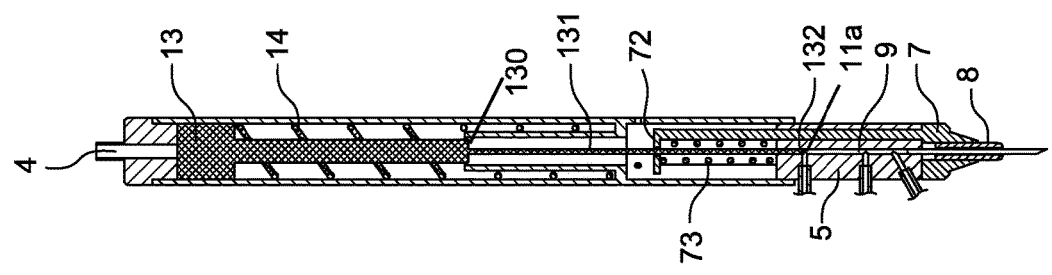

FIGS. 4A-4C are sectional views of the device of FIGS. 1, 2, 3A and 3B, and illustrate the position of the constituent elements in the rest position and in the action position. In the rest position, illustrated in FIG. 4A, the piston 13 is held in the rear position by the spring 14 and the skin stop 7 is kept in the retracted position relative to the intermediate reservoir 5 by a small compression spring 73. The end free 132 of the rod 131 is in the rear position in the channel 9 containing a graft (not shown) facing the orifice 11a.

When a source of compressed air is applied at the connection 4, the piston 13 will be mobilized forward in the body 2 until the stop 130 comes into contact with the posterior end 72 of the skin stop 7. During the same time, the end 132 has pushed the hair graft (not shown) as far as the needle 6. The piston 13 still continuing its stroke until the stop 22 of the body 2 will firstly move forward the skin stop 7 and its stop head 8 relative to the intermediate reservoir 5 (over a distance of approximately 10 mm) and at the same time move the end 132 of the rod 131 up to the free end of the needle 6 and release the hair graft (not shown) outside the needle 6. It should be understood that the displacement in front of the skin stop 7 is a relative displacement relative to all the fixed elements of the body 2 of the implantation device and that if the skin stop 7 as well as its stop head 8 are held on a fixed plane such as for example the skin plane, this will result in a movement of the body 2 back relative to the skin plane when the skin stop is pushed forward as illustrated in FIG. 4C and in more detail in FIG. 5E.

FIGS. 5A-5F are sectional views illustrating different successive stages respectively of the loading of a hair graft into the implantation instrument of FIG. 1 as well as of the implantation of the hair graft into the skin. More specifically, these figures are detailed views in partial section illustrating the different successive stages respectively of the loading of a hair graft into the implantation instrument as well as of the implantation of the graft into the scalp according to a first mode of use according to the disclosure.

In FIGS. 5A-5F, the implantation instrument is respectively connected remotely to a hair graft container (see FIGS. 8 and 9) containing at least one graft by the tube 101, the free end of which is placed in contact with a graft for its aspiration. Tubing 110 is remotely connected to a vacuum source (see FIGS. 8 and 9) operating continuously. Tubing 120 is remotely connected to a differential pressure detector (see FIGS. 8 and 9) acting as a contactor. The implantation instrument 1 is positioned above the skin or the bald scalp 55. In this rest position, the needle 6 being outside the skin, an air flow is continuously moving inside of the needle 6, the beveled end of which is in the open air, as well as in the central channel 9 via the tube 110 connected to the vacuum source. The introduction of the needle 6 into the scalp will obstruct the tip of the needle and cause a sudden reduction in pressure respectively in the channel 9 propagating at a distance to the free end of the tubing 101 causing the instant aspiration of the graft 56 traveling respectively in the tubing 101, in the oblique front channel 10, in the central channel 9 to stop in contact with the free end 132 of the rod 131 near the posterior channel 11 as illustrated in FIGS. 5B and 5C. The blocking of the graft 56 in the central channel 9 will cause a sudden variation in pressure between the orifices 12a and 11a transmitted via the tubes 120 and 110 to the differential pressure detector as illustrated further in FIG. 8. The detection of the pressure variation is an indicator of the presence and proper positioning of the hair graft 56 in the central channel 9. This presence can be expressed by an audible, visual or electronic control signal to go to the next step consisting of pressurization the connection means 4 as described in FIG. 8, causing the displacement of the rod 131 pushing the graft 56 along the central channel 9 as far as the needle 6 to finally cause the withdrawal of the latter from the scalp 55 by the through the skin stop 8 leaving in place the graft 56 perfectly positioned in the scalp as illustrated in FIGS. 5D, 5E and 5F. Stopping the pressurization at connection 4 will cause the piston to return to its initial rest position, and the implantation instrument is ready to load and implant the next graft according to the same repetitive cycle and so on.

FIG. 6A and FIG. 6B are partial detail views of the front part of the implantation device of FIG. 1 in the rest position and in the action position. In the rest position (FIG. 6A), the movable piece of conical shape acting as a skin abutment 7 is in contact with the intermediate reservoir. In the action position, the movable piece of conical shape acting as a skin abutment 7 is moved away from the intermediate reservoir in an axial direction by a rigid axis 71.

FIG. 7 is a detailed perspective view of the implantation head and the skin abutment device according to the embodiment of FIGS. 1, 2, 3A, 3B, 4A-4C, 5A-5F, 6A and 6B.

System

An embodiment of the instant disclosure relates to a system for implanting a hair graft, including: a device for implanting a hair graft; a source of pressure operably coupled to a posterior plug of the device; a hair graft container operably coupled to an anterior opening of the device; a vacuum source operably coupled to a posterior opening of the device; and a controller in communication with the source of pressure, the hair graft container, and the vacuum source. In such an embodiment, the device includes: an elongated body having an internal channel and a posterior plug configured to be operably coupled to a tube; an intermediate reservoir operably coupled to an anterior end of the elongated body and extending axially therefrom. The intermediate reservoir includes: an internal longitudinal central axis channel stretching over an entire length of the intermediate reservoir, the internal longitudinal central axis channel being fluidly connected at a posterior end to an anterior end of the internal channel, and being configured to accept and contain a hair graft; an anterior opening disposed on the intermediate reservoir and proximal to an anterior end of the intermediate reservoir; an anterior channel configured to allow a passage of the hair graft from the anterior opening and through an anterior orifice to the internal longitudinal channel; a posterior opening disposed on the intermediate reservoir and anterior to a posterior end of the intermediate reservoir; and a posterior channel configured to open into the internal longitudinal central axis channel from the posterior opening and through a posterior orifice. The device also includes a skin abutment piece movably coupled to the anterior end of the intermediate reservoir; and a hollow needle operably coupled to an anterior end of the skin abutment piece. The skin abutment piece is configured to allow passing of the hair graft from the internal longitudinal central axis channel to a lumen of the hollow needle, the elongated body further includes an actuatable rectilinear rod in the internal channel, the actuatable rectilinear rod being of a sufficient length to slide from the internal longitudinal central axis channel over an entire length of the hollow needle, the actuatable rectilinear rod being movable between a first position for facilitating loading of the hair graft into the internal longitudinal central axis channel where the posterior orifice is partially obstructed by an anterior end of the actuatable rectilinear rod, and a second position where the anterior end of the actuatable rectilinear rod occupies the lumen of the hollow needle, and the actuatable rectilinear rod, when in the second position, is configured to displace the hair graft from the internal longitudinal central axis channel, through the lumen, and through a tip of the hollow needle.

An embodiment of the disclosure relates to the system above, where the vacuum source is configured to create a vacuum in the longitudinal central axis channel such that the hair graft is passaged from the hair graft container, through the anterior opening, through the anterior orifice, and into the internal longitudinal channel upon obstruction of the tip of the hollow needle.

An embodiment of the disclosure relates to the system above, where the intermediate reservoir further includes: an accessory opening disposed on the intermediate reservoir and between the anterior opening and the posterior opening; and an accessory channel configured to open perpendicularly into the internal longitudinal central axis channel from the accessory opening and through an accessory orifice.

An embodiment of the disclosure relates to the system above, further including a differential pressure detector operably coupled to the accessory opening, and where the controller is further configured to be in communication with the source of pressure, the hair graft container, the vacuum source, and the differential pressure detector.

An embodiment of the disclosure relates to the system above, where the differential pressure detector is configured to detect whether the hair graft is present in the internal longitudinal central axis channel at least in part by detecting a variation in pressure between the accessory orifice and the posterior orifice.

An embodiment of the disclosure relates to the system above, where the system is further configured to notify a user whether the hair graft is present in the internal longitudinal central axis channel.

An embodiment of the disclosure relates to the system above, where the differential pressure detector is configured to communicate with the controller whether the hair graft is present in the internal longitudinal central axis channel, and where based on a positive detection of the hair graft in the internal longitudinal central axis channel, the controller is configured to activate the source of pressure to actuate the actuatable rectilinear rod to the second position where the anterior end of the actuatable rectilinear rod occupies the lumen of the hollow needle, and where the actuatable rectilinear rod, when in the second position, displaces the hair graft from the internal longitudinal central axis channel, through the lumen, and through the tip of the hollow needle.

An embodiment of the disclosure relates to the system above, where the skin abutment piece is further configured to at least partially aid in withdrawing the hollow needle from a scalp following implanting of the hair graft into the scalp.

An embodiment of the disclosure relates to the system above, where the hair graft container is operably coupled to the anterior opening including a robotic system, where the robotic system is in communication with the controller and is configured to mediate transport of the hair graft from the hair graft container into the internal longitudinal channel.

An embodiment of the instant disclosure herein relates to a system for implanting a hair graft. The system includes a device for implanting a hair graft, having: an elongated body including an internal channel and a posterior plug configured to be operably coupled to a tube; an intermediate reservoir operably coupled to an anterior end of the elongated body and extending axially therefrom. In such an embodiment, the intermediate reservoir includes: an internal longitudinal central axis channel stretching over an entire length of the intermediate reservoir, the internal longitudinal central axis channel being fluidly connected at a posterior end to an anterior end of the internal channel, and being configured to accept and contain a hair graft; an anterior opening disposed on the intermediate reservoir and proximal to an anterior end of the intermediate reservoir; an anterior channel configured to allow a passage of the hair graft from the anterior opening and through an anterior orifice to the internal longitudinal channel; a posterior opening disposed on the intermediate reservoir and anterior to a posterior end of the intermediate reservoir; a posterior channel configured to open perpendicularly into the internal longitudinal central axis channel from the posterior opening and through a posterior orifice; an accessory opening disposed on the intermediate reservoir and between the anterior opening and the posterior opening; and an accessory channel configured to open perpendicularly into the internal longitudinal central axis channel from the accessory opening and through an accessory orifice. The device also includes a skin abutment piece movably coupled to the anterior end of the intermediate reservoir; and a beveled hollow needle operably coupled to an anterior end of the skin abutment piece. In such an embodiment, the skin abutment piece is configured to allow passing of the hair graft from the internal longitudinal central axis channel to a lumen of the beveled hollow needle, the elongated body further includes an actuatable rectilinear rod in the internal channel, the actuatable rectilinear rod being of a sufficient length to slide from the internal longitudinal central axis channel over an entire length of the beveled hollow needle, the actuatable rectilinear rod being movable between a first position for facilitating loading of the hair graft into the internal longitudinal central axis channel where the posterior orifice is partially obstructed by an anterior end of the actuatable rectilinear rod, and a second position where the anterior end of the actuatable rectilinear rod occupies the lumen of the beveled hollow needle, and the actuatable rectilinear rod, when in the second position, is configured to displace the hair graft from the internal longitudinal central axis channel, through the lumen, and through a tip of the beveled hollow needle. The system also includes a source of pressure operably coupled to the posterior plug; a hair graft container operably coupled to the anterior opening; a vacuum source operably coupled to the posterior opening; a differential pressure detector operably coupled to the accessory opening; and a controller in communication with the source of pressure, the hair graft container, the vacuum source, and the differential pressure detector.

An embodiment of the instant disclosure herein relates to the system discussed above, where the vacuum source is continually active and creates a vacuum in the longitudinal central axis channel such that the hair graft is passaged from the hair graft container, through the anterior opening, through the anterior orifice, and into the internal longitudinal channel upon obstruction of the tip of the beveled hollow needle.

An embodiment of the instant disclosure herein relates to the system discussed above, where the differential pressure detector is configured to detect whether the hair graft is present in the internal longitudinal central axis channel at least in part by detecting a variation in pressure between the accessory orifice and the posterior orifice.

An embodiment of the instant disclosure herein relates to the system discussed above, where the pressure detector is configured to communicate with the controller whether the hair graft is present in the internal longitudinal central axis channel, and where based on a positive detection of the hair graft in the internal longitudinal central axis channel, the controller is configured to activate the source of pressure to actuate the actuatable rectilinear rod to the second position where the anterior end of the actuatable rectilinear rod occupies the lumen of the beveled hollow needle, and where the actuatable rectilinear rod, when in the second position, displaces the hair graft from the internal longitudinal central axis channel, through the lumen, and through the tip of the beveled hollow needle.

An embodiment of the instant disclosure herein relates to the system discussed above, where the hair graft container is operably coupled to the anterior opening including a robotic system, where the robotic system is in communication with the controller and is configured to mediate transport of the hair graft from the hair graft container into the internal longitudinal channel.

Figure 8:
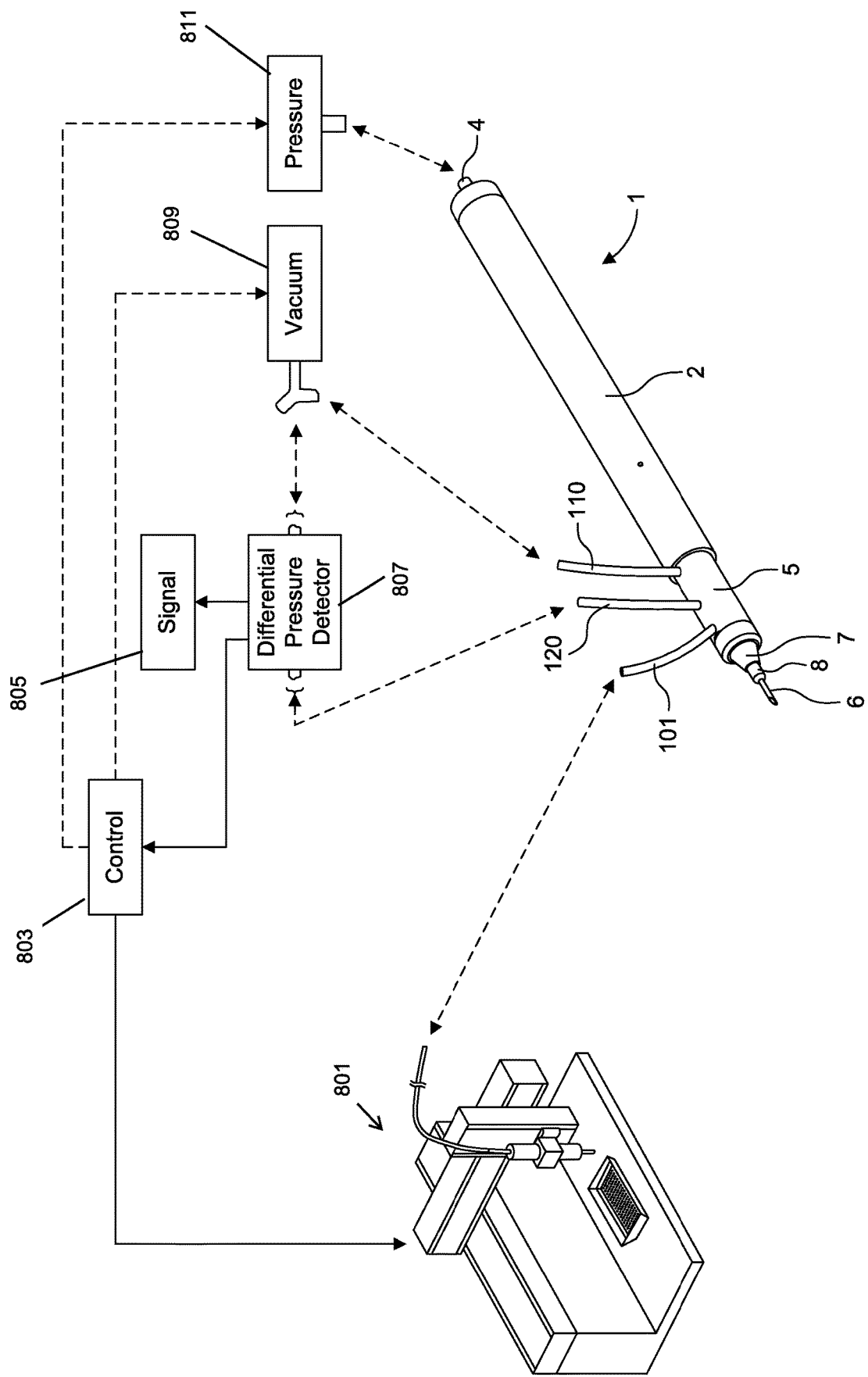
FIG. 8 is a perspective view illustrating a first mode of use of a system for implanting hair grafts into a scalp according to an embodiment of the disclosure with a robot according to a predefined program.

FIG. 8 is a perspective view illustrating a first mode of use of a system for implanting hair grafts into a scalp according to an embodiment of the disclosure with a robot according to a predefined program. The system of FIG. 8 includes an implantation device 1 according an embodiment of the disclosure having an elongated body 2 of hollow cylindrical shape having a posterior plug and a connection means 4 to a tube (not shown) connected to a pressure source. In some embodiments, the pressure source is a source of compressed air. The device 1 has, at its front, a piece of cylindrical shape acting as an intermediate reservoir 5 of a graft extended axially in front by a beveled hollow needle 6. The intermediate reservoir 5 is extended forward by a movable piece of conical shape acting as a skin abutment 7 by means of a hollow screw acting as a skin abutment head 8 adjustable relative to the part 7. The intermediate reservoir 5 has over its entire length a longitudinal central axial channel of cylindrical shape, the diameter is suitable for receiving and containing a hair graft. The reservoir 5 has at its front part a first oblique anterior channel, suitable for the passage of a graft opening into the central channel through an orifice of diameter substantially identical to that of the central channel. The reservoir 5 has at its rear part a second rear channel opening perpendicularly into the central channel through an orifice. The reservoir 5 has a third accessory channel located between the oblique channel and the posterior channel. The accessory channel opens perpendicularly into the central channel through an orifice. The orifices and are spaced a minimum distance "I" greater than the length of a graft, or approximately 10 mm. The oblique anterior channel is connected at a distance by a flexible tube 101 to a hair graft reservoir. In some embodiments, the hair graft reservoir is operably coupled to the anterior opening with a robotic system. In such an embodiment, the robotic system is in communication with a controller and is configured to mediate transport of a hair graft from the hair graft reservoir into the intermediate reservoir 5.

In the system of FIG. 8, the posterior channel is connected remotely by a flexible tube 110 to a vacuum source 809. An accessory channel is connected remotely by a flexible tube 120 to a differential pressure detector 807 connected to the tube 110. The vacuum source 809 is continually active and creates a vacuum in a longitudinal central axis channel of the intermediate reservoir 5, such that a hair graft is passaged (aspirated) from the hair graft reservoir 801 into the intermediate reservoir 5 upon obstruction of the tip of the beveled hollow needle 6. In some embodiments, the vacuum source 809 is not continually active, and instead opened on demand by an operator actioning a foot pedal with at least two levels. In such an embodiment, the first level (soft) commands a solenoid valve for the vacuum; the second level (harder) commands air compression to move the hair graft into the scalp.

In some embodiments, the hair grafts are stored in a hydration solution while in the hair graft reservoir 801. The differential pressure detector 807 is configured to detect whether the hair graft is present in the internal longitudinal central axis channel of the intermediate reservoir 5 at least in part by detecting a variation in pressure between an accessory orifice and a posterior orifice of the intermediate reservoir. This variation in pressure between the accessory orifice and the posterior orifice of the intermediate reservoir acts as a signal 805, and the pressure detector 811 is also configured to communicate this signal 805 with a controller 803 to indicate whether the hair graft is present in the internal longitudinal central axis channel of the intermediate reservoir 5. Based on a positive detection of the hair graft in the internal longitudinal central axis channel, the controller 803 is configured to activate the source of pressure 811 to actuate an actuatable rectilinear rod to a second position where an anterior end of the actuatable rectilinear rod occupies the lumen of the beveled hollow needle, and where the actuatable rectilinear rod, when in the second position, displaces the hair graft from the internal longitudinal central axis channel, through the lumen, and through the tip of the beveled hollow needle.

Figure 9:
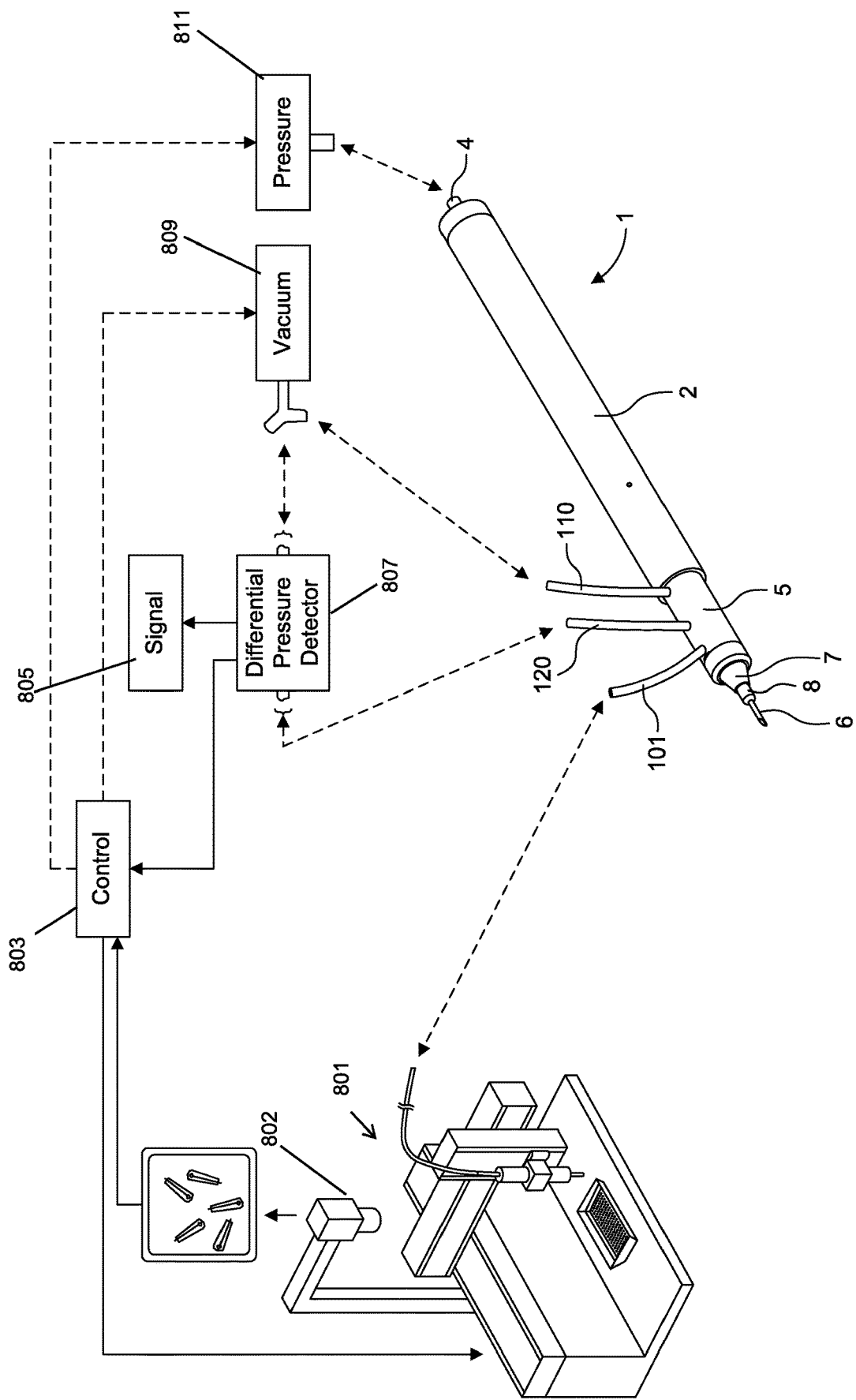
FIG. 9 is a perspective view illustrating another mode of use of a system for implanting hair grafts into a scalp according to an embodiment of the disclosure with a robot provided with a device for locating grafts by vision.

FIG. 9 is a perspective view illustrating another mode of use of the system of FIG. 8 for implanting hair grafts into a scalp according to an embodiment of the disclosure. In such a mode of use, the robotic system used to mediate transport of a hair graft from the hair graft reservoir into the intermediate reservoir 5 includes an optical system 802 for locating grafts by vision. In the system of FIG. 9, the posterior channel is connected remotely by a flexible tube 110 to a vacuum source 809. An accessory channel is connected remotely by a flexible tube 120 to a differential pressure detector 807 connected to the tube 110. The vacuum source 809 is continually active and creates a vacuum in a longitudinal central axis channel of the intermediate reservoir 5, such that a hair graft is passaged from the hair graft reservoir 801 into the intermediate reservoir 5 upon obstruction of the tip of the beveled hollow needle 6. In some embodiments, the vacuum source 809 is not continually active, and instead opened on demand by an operator actioning a foot pedal with at least two levels. In such an embodiment, the first level (soft) commands a solenoid valve for the vacuum; the second level (harder) commands air compression to move the hair graft into the scalp.

An optical system 802 operably coupled to the hair graft reservoir 801 identifies a hair graft to be inserted and then assists in the accurate transport of the hair graft to the intermediate reservoir 5. The differential pressure detector 807 is configured to detect whether the hair graft is present in the internal longitudinal central axis channel of the intermediate reservoir 5 at least in part by detecting a variation in pressure between an accessory orifice and a posterior orifice of the intermediate reservoir. This variation in pressure between the accessory orifice and the posterior orifice of the intermediate reservoir acts as a signal 805, and the pressure detector 811 is also configured to communicate this signal 805 with a controller 803 to indicate whether the hair graft is present in the internal longitudinal central axis channel of the intermediate reservoir 5. Based on a positive detection of the hair graft in the internal longitudinal central axis channel, the controller 803 is configured to activate the source of pressure 811 to actuate an actuatable rectilinear rod to a second position where an anterior end of the actuatable rectilinear rod occupies the lumen of the beveled hollow needle, and where the actuatable rectilinear rod, when in the second position, displaces the hair graft from the internal longitudinal central axis channel, through the lumen, and through the tip of the beveled hollow needle.

Figure 10B:
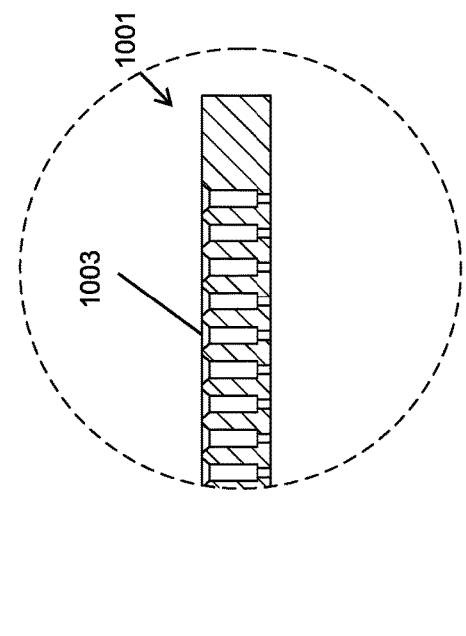
FIGS. 10, 10A, 10B, and 10C are views of a hair graft storage tray according to an embodiment of the disclosure.
Figure 10C:
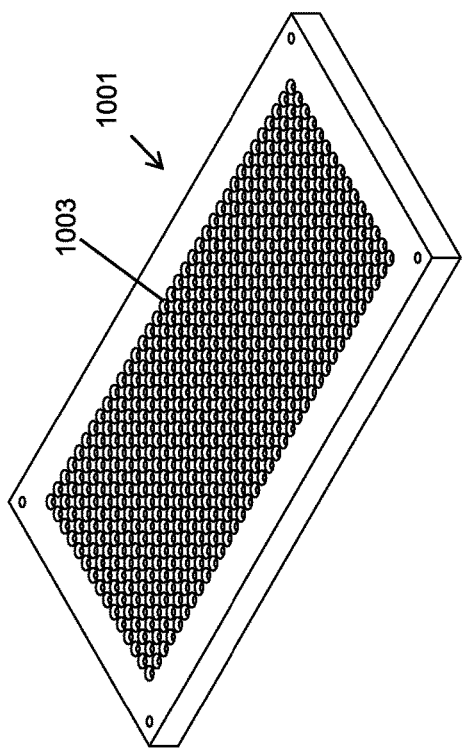
Figure 10:
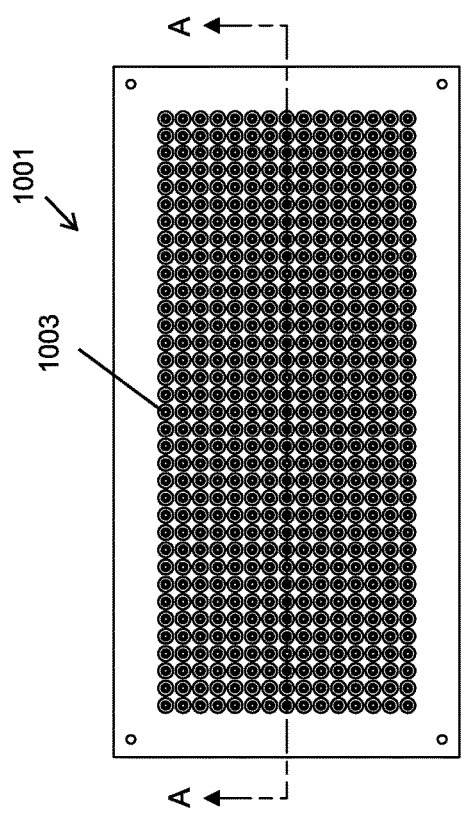

FIGS. 10, 10A, 10B, and 10C are views of a hair graft storage tray 1001 according to an embodiment of the disclosure. In some embodiments, the hair graft storage tray 1001 is configured to be operably coupled to a hair graft reservoir, such as the hair graft reservoir 801 of the system of FIG. 8 or FIG. 9. FIG. 10 is a top view of the hair graft storage tray 1001 showing a top view of several hair graft storage wells 1003. Each of the hair graft storage wells is configured to house one or more hair grafts that are to be transported to a device for implanting hair grafts. In some embodiments, each of the hair graft storage wells is configured to house one hair graft. The hair graft storage wells 1003 are further configured to ensure that the hair grafts are properly oriented. In some embodiments, proper orientation includes storage of the hair grafts in a root-down orientation.

Figure 10A:
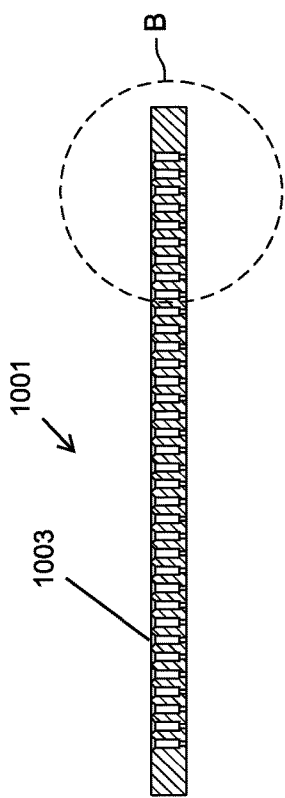

FIG. 10A is a sectional view of the hair graft storage tray of FIG. 10 along the A-A axis. FIG. 10B is a zoomed-in view of the "B" region indicated in FIG. 10A. FIG. 10C is a perspective view of the hair graft storage tray.

Figure 11C:
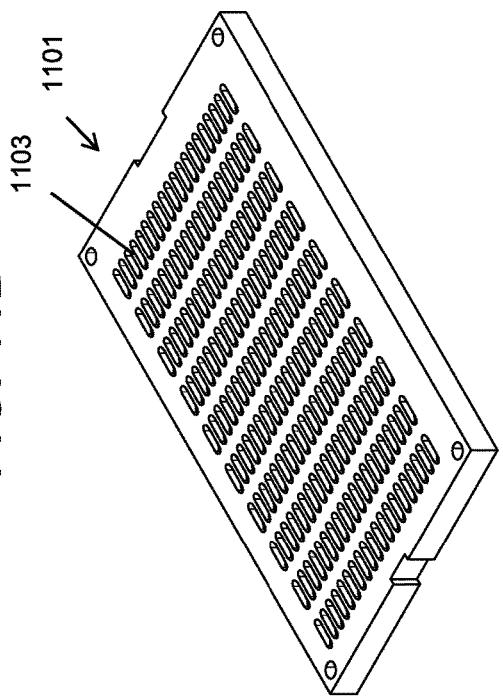
FIGS. 11, 11A, 11B, and 11C are views of a second embodiment of a graft storage tray according to the disclosure.
Figure 11B:
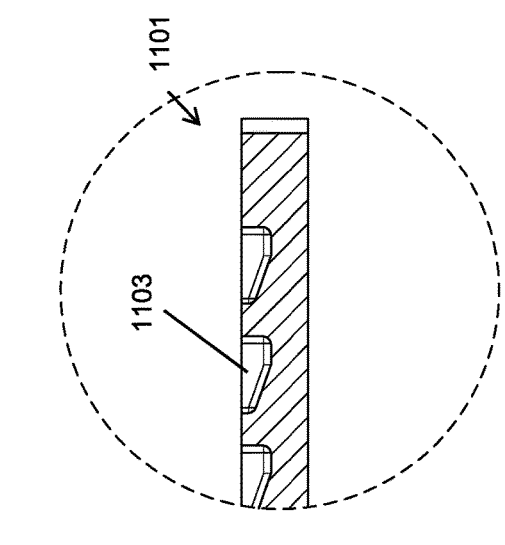
Figure 11:
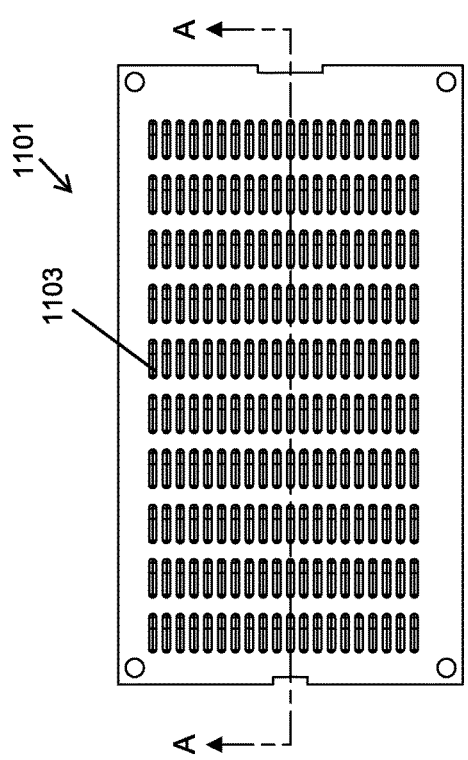
Figure 11A:
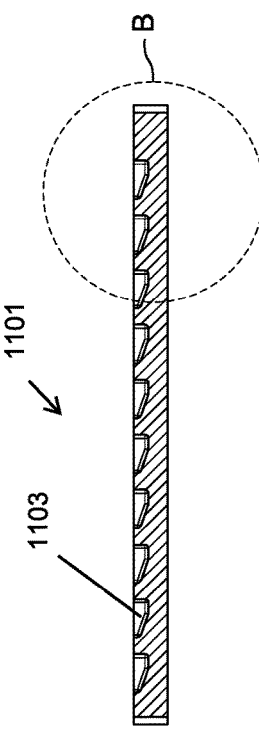

FIGS. 11, 11A, 11B, and 11C are views of a second embodiment of a hair graft storage tray 1101 according to the disclosure. In some embodiments, the hair graft storage tray 1101 is configured to be operably coupled to a hair graft reservoir, such as the hair graft reservoir 801 of the system of FIG. 8 or FIG. 9. FIG. 11 is a top view of the hair graft storage tray 1101 showing a top view of several hair graft storage wells 1103. Each of the hair graft storage wells is configured to house one or more hair grafts that are to be transported to a device for implanting hair grafts. In some embodiments, each of the hair graft storage wells is configured to house one hair graft. The hair graft storage wells 1103 are further configured to ensure that the hair grafts are properly oriented. In some embodiments, proper orientation includes storage of the hair grafts in a root-down orientation. FIG. 11A is a sectional view of the hair graft storage tray of FIG. 11 along the A-A axis. FIG. 11B is a zoomed-in view of the "B" region indicated in FIG. 11A. FIG. 11C is a perspective view of the hair graft storage tray.

Methods

An embodiment of the disclosure relates to a method for implanting a hair graft into a scalp using a device for implanting a hair graft, including: creating a vacuum in the longitudinal central axis channel; obstructing the hollow needle; loading the hair graft into the internal longitudinal central axis channel including passaging the hair graft from a hair graft container, through the anterior opening, through the anterior orifice, and into the internal longitudinal channel; detecting the hair graft in the internal longitudinal central axis channel; and actuating the actuatable rectilinear rod such that the actuatable rectilinear rod displaces the hair graft from the internal longitudinal central axis channel, through the lumen, and through the tip of the hollow needle. In such an embodiment, the device includes: an elongated body having an internal channel and a posterior plug configured to be operably coupled to a tube; an intermediate reservoir operably coupled to an anterior end of the elongated body and extending axially therefrom. The intermediate reservoir includes: an internal longitudinal central axis channel stretching over an entire length of the intermediate reservoir, the internal longitudinal central axis channel being fluidly connected at a posterior end to an anterior end of the internal channel, and being configured to accept and contain a hair graft; an anterior opening disposed on the intermediate reservoir and proximal to an anterior end of the intermediate reservoir; an anterior channel configured to allow a passage of the hair graft from the anterior opening and through an anterior orifice to the internal longitudinal channel; a posterior opening disposed on the intermediate reservoir and anterior to a posterior end of the intermediate reservoir; and a posterior channel configured to open into the internal longitudinal central axis channel from the posterior opening and through a posterior orifice. The device also includes a skin abutment piece movably coupled to the anterior end of the intermediate reservoir; and a hollow needle operably coupled to an anterior end of the skin abutment piece. The skin abutment piece is configured to allow passing of the hair graft from the internal longitudinal central axis channel to a lumen of the hollow needle, the elongated body further includes an actuatable rectilinear rod in the internal channel, the actuatable rectilinear rod being of a sufficient length to slide from the internal longitudinal central axis channel over an entire length of the hollow needle, the actuatable rectilinear rod being movable between a first position for facilitating loading of the hair graft into the internal longitudinal central axis channel where the posterior orifice is partially obstructed by an anterior end of the actuatable rectilinear rod, and a second position where the anterior end of the actuatable rectilinear rod occupies the lumen of the hollow needle, and the actuatable rectilinear rod, when in the second position, is configured to displace the hair graft from the internal longitudinal central axis channel, through the lumen, and through a tip of the hollow needle.

An embodiment of the disclosure relates to the method above, where the obstructing the hollow needle includes inserting the beveled hollow needle into the scalp.

An embodiment of the disclosure relates to the method above, further including a step of withdrawing the hollow needle from the scalp following the actuating the actuatable rectilinear rod, where the withdrawing the hollow needle is at least partially mediated by the skin abutment piece.

An embodiment of the disclosure relates to a method for implanting a hair graft into an implantation depth at an implantation site in a patient's scalp using a device, the method including: inserting at least a portion of a hollow needle from the device into the implantation site while a skin abutment piece from the device is in a first position; actuating a rod from the device such that the hair graft is advanced through the hollow needle while the hollow needle is inserted to the implantation depth at the implantation site and while the skin abutment piece is in the first position; and withdrawing the hollow needle from the implantation site including moving the skin abutment piece to a second position.

An embodiment of the disclosure relates to a method for implanting a hair graft into an implantation depth at an implantation site in a patient's scalp using a device, the method including: loading the hair graft into a reservoir of the device; inserting at least a portion of a hollow needle of the device into the implantation site; actuating a rod of the device such that the hair graft is advanced through the hollow needle while the hollow needle is inserted to the implantation depth at the implantation site; and withdrawing the hollow needle from the implantation site. In such an embodiment, loading of said hair graft includes aspiration of the hair graft into the reservoir at least partially in response to placement of the hollow needle adjacent the patient's scalp, and actuating the movable rod is performed at least partially in response to an indication from a detector of the device that the hair graft is aspirated to the reservoir response.

An embodiment of the disclosure relates to a method of implanting a hair graft using the devices or systems described above. An example embodiment of a method includes at least the following steps, as seen in FIGS. 5A-5F. As seen in FIG. 5A, an implantation instrument 1 is positioned above a scalp 55. In this rest position, the needle 6 being outside the skin, an air flow is continuously moving inside of a needle 6, a beveled end of which is in the open air, as well as in a central channel 9 via the tube 110 connected to a vacuum source. As the needle is introduced into the scalp (FIG. 5B), the tip of the needle becomes obstructed, causing aspiration of the hair graft 56 through the tubing 101, through an oblique front channel 10, and into the central channel 9. The hair graft stops when it contacts a free end 132 of a rod 131 near a posterior channel 11 (see FIGS. 5B and 5C). The blocking of the graft 56 in the central channel 9 causes a sudden variation in pressure between an orifice 12a and an orifice 11a, which is transmitted via tubes 120 and 110 to a differential pressure detector. The detection of the pressure variation is an indicator of the presence and proper positioning of the hair graft 56 in the central channel 9. Next, a connection means is pressurized by an external pressure source, causing the displacement of a rod 131 pushing the hair graft 56 along the central channel 9 as far as the needle 6 to finally cause the withdrawal of the implantation device 1 from the scalp 55, leaving in place the hair graft 56 in the scalp as illustrated in FIGS. 5D, 5E and 5F. Stopping the pressurization at the connection means will cause a piston to return to its initial rest position, and the implantation instrument is ready to load and implant the next graft according to the same repetitive cycle and so on.

The embodiments illustrated and discussed in this specification are intended only to teach those skilled in the art how to make and use the disclosure herein. In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. A device for implanting a hair graft, comprising:
   an elongated body comprising an internal channel and a posterior plug configured to be operably coupled to a tube;
   an intermediate reservoir operably coupled to an anterior end of said elongated body and extending axially therefrom, said intermediate reservoir comprising:
      an internal longitudinal central axis channel stretching over an entire length of said intermediate reservoir, said internal longitudinal central axis channel being fluidly connected at a posterior end to an anterior end of said internal channel, and being configured to accept and contain a hair graft;
      an anterior opening disposed on said intermediate reservoir and proximal to an anterior end of said intermediate reservoir;
      an anterior channel configured to allow a passage of said hair graft from said anterior opening and through an anterior orifice to said internal longitudinal channel;
      a posterior opening disposed on said intermediate reservoir and anterior to a posterior end of said intermediate reservoir; and
      a posterior channel configured to open into said internal longitudinal central axis channel from said posterior opening and through a posterior orifice;
   a skin abutment piece movably coupled to said anterior end of said intermediate reservoir; and
   a hollow needle operably coupled to an anterior end of said skin abutment piece,
   wherein said skin abutment piece is configured to allow passing of said hair graft from said internal longitudinal central axis channel to a lumen of said hollow needle,
   wherein said elongated body further comprises an actuatable rectilinear rod in said internal channel, said actuatable rectilinear rod being of a sufficient length to slide from said internal longitudinal central axis channel over an entire length of said hollow needle, said actuatable rectilinear rod being movable between a first position for facilitating loading of said hair graft into said internal longitudinal central axis channel where said posterior orifice is partially obstructed by an anterior end of said actuatable rectilinear rod, and a second position during an implantation cycle of said hair graft where said anterior end of said actuatable rectilinear rod occupies said lumen of said hollow needle,
   wherein said actuatable rectilinear rod, when in said second position, is configured to displace said hair graft from said internal longitudinal central axis channel, through said lumen, and through a tip of said hollow needle, and
   wherein said actuatable rectilinear rod and said skin abutment piece are configured to move independently during at least part of the implantation cycle.

2. The device of claim 1, wherein said intermediate reservoir further comprises:
   an accessory opening disposed on said intermediate reservoir and between said anterior opening and said posterior opening; and
   an accessory channel configured to open perpendicularly into said internal longitudinal central axis channel from said accessory opening and through an accessory orifice.

3. The device of claim 2, wherein said posterior opening and said accessory opening are spaced at least 10 mm apart.

4. The device of claim 1, wherein said posterior channel is configured to open perpendicularly into said internal longitudinal central axis channel from said posterior opening and through a posterior orifice.

5. The device of claim 1, wherein said hollow needle is a beveled hollow needle.

6. The device of claim 1, wherein said intermediate reservoir further comprises a hollow slide stretching over an entire length of said intermediate reservoir, and
   wherein said skin abutment piece is movably coupled to said anterior end of said intermediate reservoir comprising a rigid axial slide, said rigid axial slide being connected at an anterior end to the posterior end of said skin abutment piece, said rigid axial slide being configured to pass through said hollow slide, and said rigid axial slide being connected at a posterior end to said anterior end of said elongated body.

7. The device of claim 6, wherein moving of said actuatable rectilinear rod to said first position results in moving of said skin abutment piece to a first skin abutment piece position where said skin abutment piece is in contact with said intermediate reservoir,
   and wherein moving of said actuatable rectilinear rod to said second position results in moving of said skin abutment piece to a second skin abutment piece position where said intermediate reservoir is separated from said skin abutment piece in an axial direction by said rigid axial slide.

8. A system for implanting a hair graft, comprising:
   the device for implanting a hair graft of claim 1;
   a source of pressure operably coupled to said posterior plug;
   a hair graft container operably coupled to said anterior opening;
   a vacuum source operably coupled to said posterior opening; and
   a controller in communication with said source of pressure, said hair graft container, and said vacuum source.

9. The system of claim 8, wherein said vacuum source is configured to create a vacuum in said longitudinal central axis channel such that the hair graft is passaged from said hair graft container, through said anterior opening, through said anterior orifice, and into said internal longitudinal channel upon obstruction of said tip of said hollow needle.

10. The system of claim 8, wherein said intermediate reservoir further comprises:
- an accessory opening disposed on said intermediate reservoir and between said anterior opening and said posterior opening; and
- an accessory channel configured to open perpendicularly into said internal longitudinal central axis channel from said accessory opening and through an accessory orifice.

11. The system of claim 10, further comprising a differential pressure detector operably coupled to said accessory opening, and wherein said controller is further configured to be in communication with said source of pressure, said hair graft container, said vacuum source, and said differential pressure detector.

12. The system of claim 11, wherein said differential pressure detector is configured to detect whether said hair graft is present in said internal longitudinal central axis channel at least in part by detecting a variation in pressure between said accessory orifice and said posterior orifice.

13. The system of claim 12, wherein said system is further configured to notify a user whether said hair graft is present in said internal longitudinal central axis channel.

14. The system of claim 11, wherein said differential pressure detector is configured to communicate with said controller whether said hair graft is present in said internal longitudinal central axis channel, and wherein based on a positive detection of said hair graft in said internal longitudinal central axis channel, said controller is configured to activate said source of pressure to actuate said actuatable rectilinear rod to said second position where said anterior end of said actuatable rectilinear rod occupies said lumen of said hollow needle, and wherein said actuatable rectilinear rod, when in said second position, displaces said hair graft from said internal longitudinal central axis channel, through said lumen, and through said tip of said hollow needle.

15. The system of claim 8, wherein said skin abutment piece is further configured to at least partially aid in withdrawing said hollow needle from a scalp following implanting of said hair graft into said scalp.

16. The system of claim 8, wherein the operable coupling of the hair graft container to said anterior opening comprises a robotic system, wherein said robotic system is in communication with said controller and is configured to mediate transport of said hair graft from said hair graft container into said internal longitudinal channel.

17. The system of claim 16, wherein said robotic system includes an optical system constructed to identify and locate said hair graft by vision and to mediate transport of said hair graft from said hair graft container,
- wherein said hair graft in said hair graft container is stored in a hydration solution comprising a plurality of hair grafts, and
- wherein the plurality of hair grafts are arranged in random orientations in the hydration solution.

18. A method for implanting a hair graft into a scalp using the device of claim 1, comprising:
- creating a vacuum in said longitudinal central axis channel;
- obstructing said hollow needle;
- loading said hair graft into said internal longitudinal central axis channel comprising passaging said hair graft from a hair graft container, through said anterior opening, through said anterior orifice, and into said internal longitudinal channel;
- detecting said hair graft in said internal longitudinal central axis channel via a change in pressure at an accessory channel that opens into said internal longitudinal central axis channel; and
- actuating said actuatable rectilinear rod such that said actuatable rectilinear rod displaces said hair graft from said internal longitudinal central axis channel, through said lumen, and through said tip of said hollow needle.

19. The method of claim 18, wherein said obstructing said hollow needle comprises inserting said beveled hollow needle into said scalp.

20. The method of claim 19, further comprising a step of withdrawing said hollow needle from said scalp following said actuating said actuatable rectilinear rod, wherein said withdrawing said hollow needle is at least partially mediated by said skin abutment piece.

21. The device of claim 1, wherein said actuatable rectilinear rod has, at its posterior end, a stop which is spaced apart from a posterior end of the skin abutment piece while in the first position and which engages with the posterior end of the skin abutment piece during movement to the second position, thereby to allow said independent movement of said actuatable rectilinear rod and said skin abutment piece during at least part of the implantation cycle.

22. A device for implantation of a hair graft to an implantation depth at an implantation site in a patient's scalp comprising:
- a hollow needle through which the hair graft is implantable to the implantation site;
- a skin abutment piece at least partially around the hollow needle, the skin abutment piece being movable between a first position in which the hollow needle projects beyond the skin abutment piece by the implantation depth and a second position in which the skin abutment piece is substantially flush with a tip of the hollow needle, wherein a spring biases the skin abutment piece to the first position; and
- a rod slidably positioned inside the hollow needle and constructed to advance the hair graft through the hollow needle while the hollow needle is inserted to the implantation depth at the implantation site and while the skin abutment piece is in the first position,
- wherein the skin abutment piece is moved to the second position after implantation of the hair graft through the hollow needle to the implantation depth, so as to withdraw the hollow needle from the implantation site leaving the hair graft implanted at the implantation site at the implantation depth.

23. The device according to claim 22, further comprising a piston for advancing the rod through the needle, wherein the skin abutment piece extends longitudinally inward of the device to a posterior end thereof, and wherein the piston has a stop positioned longitudinally to engage with the posterior end of the skin abutment piece to move the skin abutment piece from the first position to the second position.

24. The device according to claim 23, wherein the piston is spring loaded so as to be biased against engagement of the stop to the posterior end of the skin abutment piece.

25. The device according to claim 24, further comprising a port constructed to receive pressurized gas so as to drive the piston against the bias of its spring loading.

26. A method for implanting a hair graft into an implantation depth at an implantation site in a patient's scalp using the device of claim 22, comprising:
- inserting at least a portion of said hollow needle into said implantation site while said skin abutment piece is in said first position;

actuating said rod such that said hair graft is advanced through the hollow needle while the hollow needle is inserted to said implantation depth at the implantation site and while said skin abutment piece is in said first position; and withdrawing said hollow needle from said implantation site comprising moving said skin abutment piece to the second position.

27. A device for implantation of a hair graft to an implantation depth at an implantation site in a patient's scalp comprising:

a reservoir constructed to receive the hair graft;

a hollow needle extending outwardly of the device from an anterior end of the reservoir;

a movable rod biased to a first position at a posterior end of the reservoir, the rod being slidably positionable inside the hollow needle and constructed to advance the hair graft through the hollow needle to the implantation depth while the hollow needle is inserted at the implantation site;

an accessory channel which opens to the interior of the reservoir, the accessory channel being positioned away from the first position toward the hollow needle at a distance substantially corresponding to at least a length of the hair graft;

a rear channel which opens to the interior of the reservoir, the rear channel being positioned substantially adjacent to the first position; and an oblique channel through which the hair graft is aspirated, the oblique channel being angled obliquely relative to the reservoir and being positioned between the accessory channel and the hollow needle, wherein a vacuum source connected to the rear channel aspirates the hair graft through the oblique channel into the reservoir responsive to placement of the hollow needle adjacent the patient's scalp, and wherein a detector connected to the accessory channel provides an indication that the hair graft is aspirated to the reservoir to detection of a pressure change at the accessory channel.

28. The device according to claim 27, wherein the indication is comprised of at least one of multiple signals including audible, visual and electronic control signals.

29. The device according to claim 27, wherein responsive to the indication, a source of pressure drives the movable rod from the first position to a second position where the hair graft is advanced through the hollow needle to the implantation depth while the hollow needle is inserted at the implantation site.

30. A method for implantation of a hair graft to an implantation depth at an implantation site in a patient's scalp using the device of claim 27, comprising:

loading said hair graft into said reservoir;

inserting at least a portion of said hollow needle into said implantation site;

actuating said rod such that said hair graft is advanced through the hollow needle while the hollow needle is inserted to said implantation depth at the implantation site; and withdrawing said hollow needle from said implantation site, wherein said loading of said hair graft comprises aspiration of said hair graft into said reservoir at least partially in response to placement of said hollow needle adjacent the patient's scalp, and wherein said actuating said movable rod is performed at least partially in response to an indication from said detector that the hair graft is aspirated to the reservoir response.

* * * * *